United States Patent [19]

Dye

[11] Patent Number: 5,240,218

[45] Date of Patent: Aug. 31, 1993

[54] RETRACTABLE SUPPORT ASSEMBLY

[75] Inventor: Leonard L. Dye, Moreno Valley, Calif.

[73] Assignee: Loma Linda University Medical Center, Loma Linda, Calif.

[21] Appl. No.: 780,627

[22] Filed: Oct. 23, 1991

[51] Int. Cl.⁵ .............................................. A61B 19/00
[52] U.S. Cl. .................. 248/330.1; 248/335; 248/333
[58] Field of Search ............... 248/669, 335, 320, 321, 248/334.1, 336, 337, 338, 333, 579, 610; 378/193, 195, 197, 198

[56] References Cited

U.S. PATENT DOCUMENTS

| | | | |
|---|---|---|---|
| 558,609 | 4/1896 | Peeples | 248/337 |
| 2,737,596 | 3/1956 | Haupt et al. | 248/333 X |
| 2,876,362 | 3/1959 | Foderaro | 248/334.1 X |
| 3,175,085 | 3/1965 | Avery | 378/197 |
| 3,556,455 | 1/1971 | Storm | 248/333 |
| 3,776,500 | 12/1973 | Foderaro | 248/333 |
| 3,986,697 | 10/1976 | Amor, Jr. et al. | 248/333 |
| 4,677,273 | 6/1987 | Colegrove et al. | 248/333 X |
| 4,901,339 | 2/1990 | Heinz et al. | 378/197 |
| 5,048,070 | 9/1991 | Maehama et al. | 378/193 X |

FOREIGN PATENT DOCUMENTS

212747  4/1968  U.S.S.R. ..................... 248/333

Primary Examiner—Karen J. Chotkowski
Attorney, Agent, or Firm—Robert R. Meads

[57] ABSTRACT

A vertically retractable support assembly comprising a plurality of telescoping sets of three or more laterally spaced vertical guide rods, the rods of each set being laterally tied at their lowermost ends to impart lateral stability to the rods thereof. The first set of rods is secured at its upper end to a stationary mount to extend vertically therefrom and support a first carrier for vertical movement on the rods thereof. The second set of rods is secured at its upper end to the first carrier to extend vertically therefrom and support a second carrier for vertical movement on the rods thereof in a telescoping manner relative to the rods of the first set, and so on. A member to be selectively positioned is secured to the lateral tie for the lowermost set of guide rods. Each carrier is urged toward a vertical retracted position by an extendable spring mechanism secured to the mount. A brake normally locks the spring mechanism to hold the carriers in their vertically retracted position. A handle including a brake release is secured to the lowermost lateral tie to permit an operator to simultaneously release the brake and pull down the carriers to an exact stop position controlled by cooperative stops on the carriers and the lateral ties where the brake may be re-engaged to secure the member in the exact stop position.

16 Claims, 6 Drawing Sheets

RETRACTABLE SUPPORT ASSEMBLY

BACKGROUND

The present invention relates to an improved vertically retractable support assembly useful, for example, in the support and exact vertical positioning of an image receptor or x-ray source in a radiation therapy system. Such support assemblies are useful in the cancer therapy system described in U.S. Pat. No. 4,870,287 and in the methods and apparatus described in U.S. patent application Ser. No. 07/332,549 filed Mar. 31, 1989, both of which are assigned to the assignee of the present invention. The Loma Linda University Medical Center, and both of which are incorporated herein by this reference.

As described in the referenced patent application, prior to proton treatment, a patient is positioned on a patient support or pod and x-rays are taken showing the position of the patient in the pod. Such position information is used to ensure continued proper positioning of the patient during treatment. Also, it is important during subsequent treatment that the patient be located in exactly the same position in the support pod. Therefore, prior to subsequent treatment, the patient is again placed in the support pod and x-rays taken and compared with the previous x-rays to determine any differences in patient position. Any differences in patient position are eliminated prior to the subsequent treatment by moving the patient in the pod and again taking and comparing x-rays. In the taking of all such x-rays it is important that the x-ray source and image receptor be in the exact same relative position in order for the x-ray information to be meaningful in determining the correct positioning and repositioning of the patient.

Prior support assemblies for image receptors have been vertically retractable usually from a ceiling mount to control the vertical position of the receptor relative to the patient. Such assemblies have comprised vertically telescoping tubes, the innermost one of the tubes carrying the image receptor. The vertical telescoping movement of the tubes is controlled either by ball bearings riding in aligned outer and inner vertical channels in the telescoping tubes or by guide rollers bearing on guide rails positioned on the outside of the telescoping tubes. The telescoping tubes are connected to a counterweight mechanism which permits an operator to slowly extend and then retract the telescoping tubes to establish the vertical position of the image receptor. Such prior vertically retractable assemblies are very costly, do not possess adequate lateral stability and are difficult to precisely maneuver to exact predetermined stops.

Accordingly, there is a need for a simplified, relatively inexpensive, laterally stable, vertically retractable support assembly which is capable of being easily maneuvered and precisely controlled to bring the assembly to exact vertical stop positions. The present invention satisfies such needs.

SUMMARY OF INVENTION

Basically, the vertically retractable support assembly of the present invention comprises a plurality of laterally stabilized telescoping sets of three or more laterally spaced vertical guide rods each supporting a carrier for smooth, low friction, vertical movement on the rods thereof. An uppermost or first one of the sets of guide rods is secured to a stationary mount to extend downward therefrom. The next upper-most or second set of guide rods is secured to the carrier supported by the first set of rods, that is the first carrier, to extend vertically downward therefrom and to telescope within the first set of guide rods upon upward movement or retraction of the second set into the first. A second one of the carriers is supported on the second set of guide rods in the same manner as the first carrier and support the next or third set of guide rods to extend vertically downward there from and to telescope within the second set upon upward movement or retraction of the third set into the second, and so forth to the lowermost or last set of guide rods. A support member for an image receptor, or x-ray source or other device or item is secured to the lowermost or last set of guide rods for smooth, precise and exact vertical positioning by an operator's downward extension of the sets of guide rods from their normally retracted and telescoped position. Such downward vertical movement is in response to the operator releasing a brake and pulling down on a handle secured to the lowermost set of guide rails in opposition to an upward spring force exerted by an extension spring mechanism secured to the stationary mount and to each of the carriers. The brake normally locks the spring mechanism against extension and retraction and upon release permits the smooth downward movement of the carrier and sets the guide rods supported thereby to a predetermined adjustable and exact vertical stop position and to hold in that position upon reactivation of the brake. For example, the exact stop position may be the vertical position of prealignment for an x-ray source and image receptor relative to a treatment source as described in the aforementioned patent application. Such smooth vertical telescoping motion is enhanced by vertical bearings in the carriers smoothly receiving the guide rods and by a speed governor for regulating the rate of extension and retraction of the spring mechanism. Further, the stopping of such smooth movement is cushioned at the exact vertical stop by shock absorbers and the occurrence of such exact positioning signaled by a sensor actuated indicator. The sensor may be in circuit with the x-ray source such that the source can only be actuated when the support assembly has reached and is releasably locked in the exact vertical position.

DETAILED DESCRIPTION OF INVENTION

Figure 1:
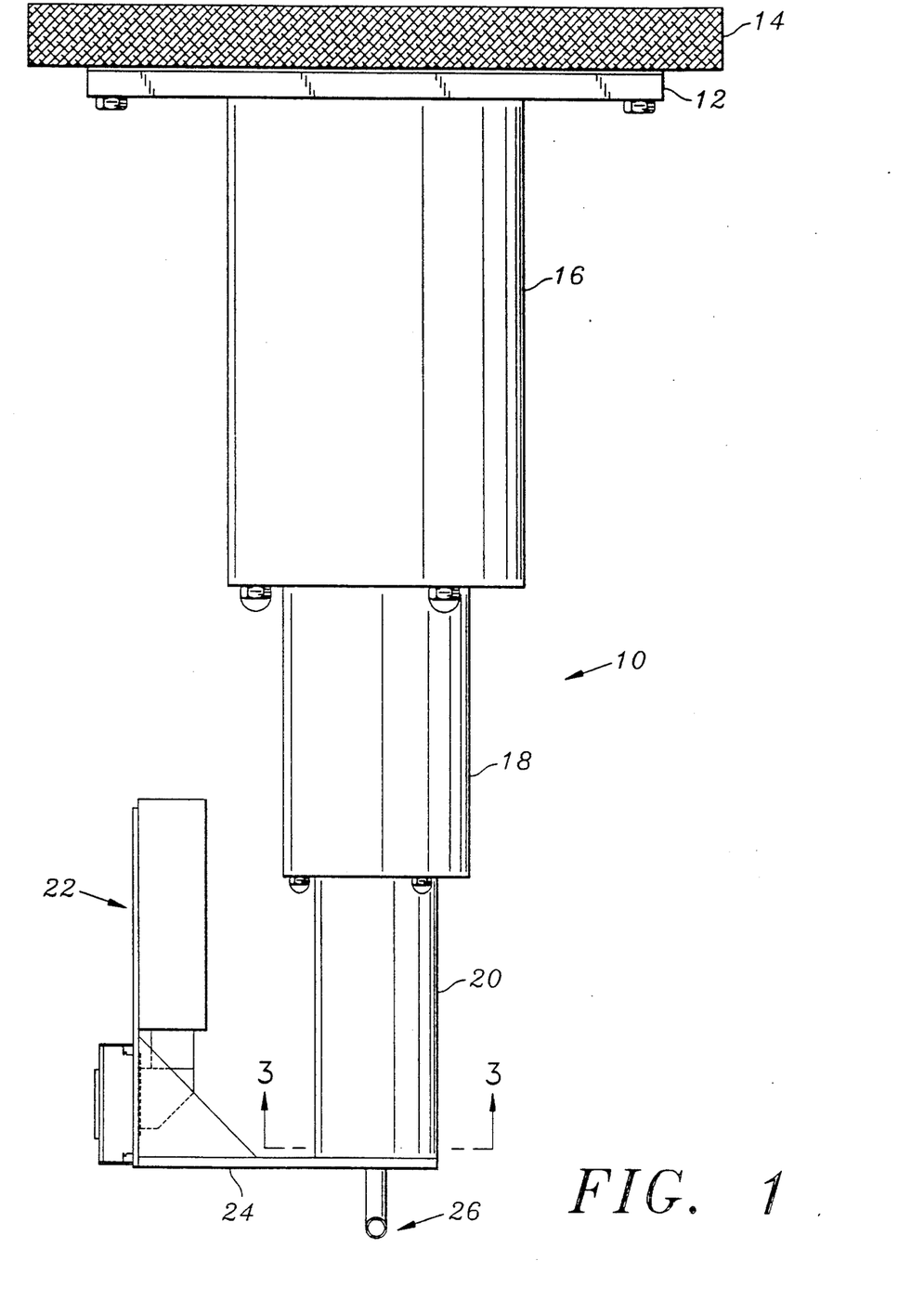
FIG. 1 is a side view of a retractable support assembly comprising a preferred form of the present invention.
Figure 3:
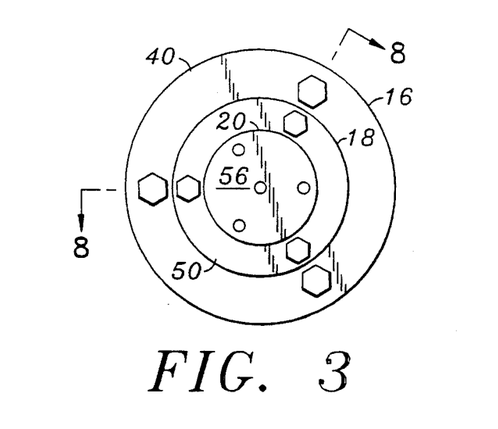
FIG. 3 is an end view of the assembly of FIG. 1 looking in the direction of the arrows 3—3.
Figure 4:
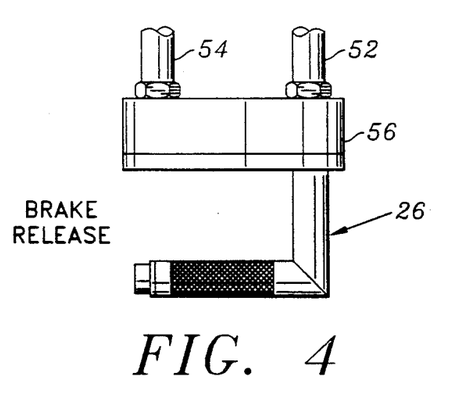
FIG. 4 is a fragmentary side view of a handle portion of the assembly of FIG. 2 looking in the direction of arrows 4—4.

As illustrated by way of example in FIGS. 1 and 3, the retractable support assembly 10 of the present invention comprises a horizontal stationary mounting plate 12 bolted to a ceiling member 14 and three telescoping tubular covers 16, 18 and 20 extending vertically from the mounting plate 12. An image receptor 22 carried by a support bracket 24 is secured at the bottom of the lowermost tubular cover 20 for alignment with an x-ray source (not shown). As will be described in greater detail hereafter, the vertical position of the image receptor 22 is manually maneuvered and precisely controlled by an operator pulling on a handle 26 extending downward from the support bracket 24.

Figure 2:
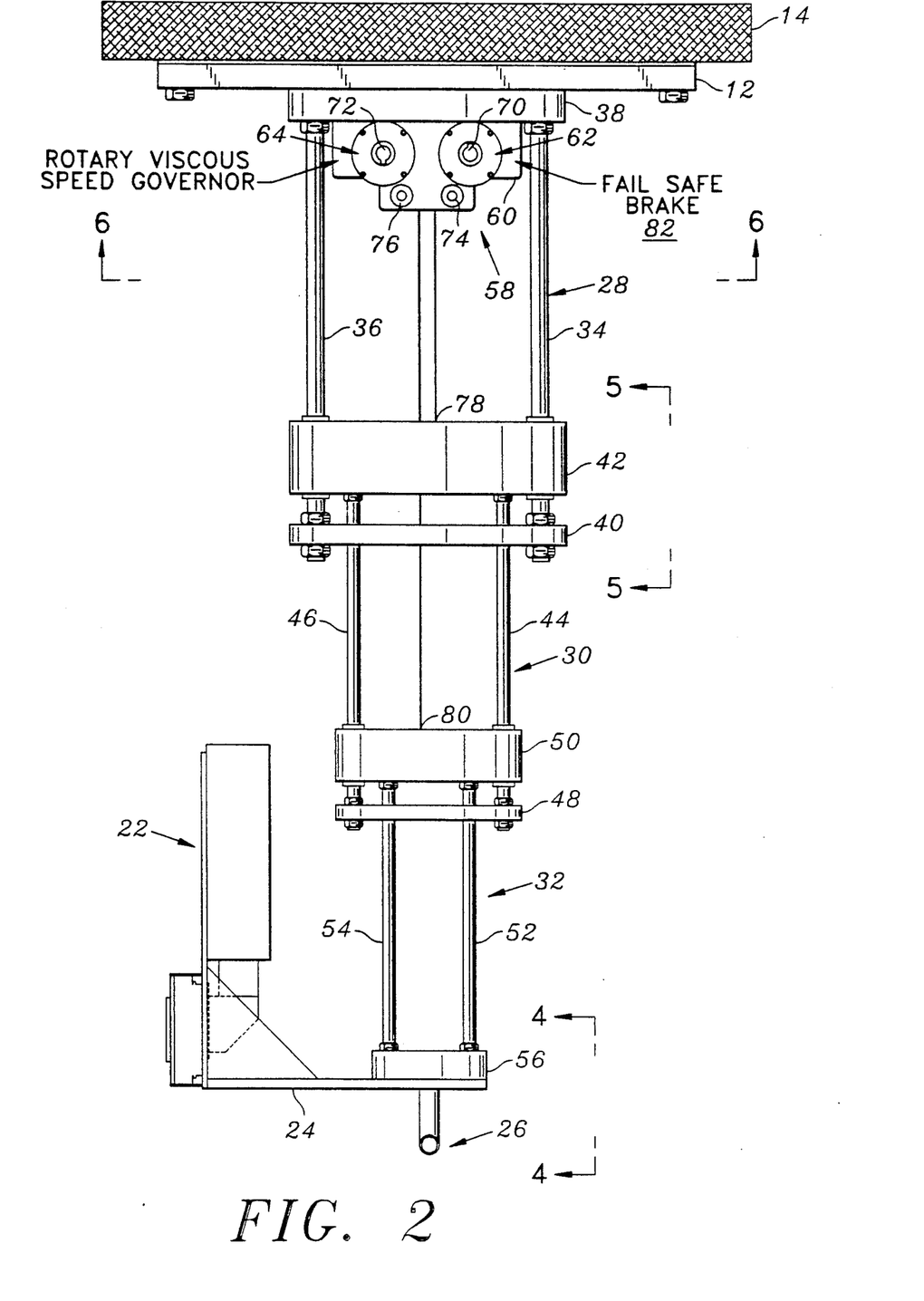
FIG. 2 is a side view of the retractable support assembly shown in FIG. 1 with the outer telescoping covers removed.
Figure 8:
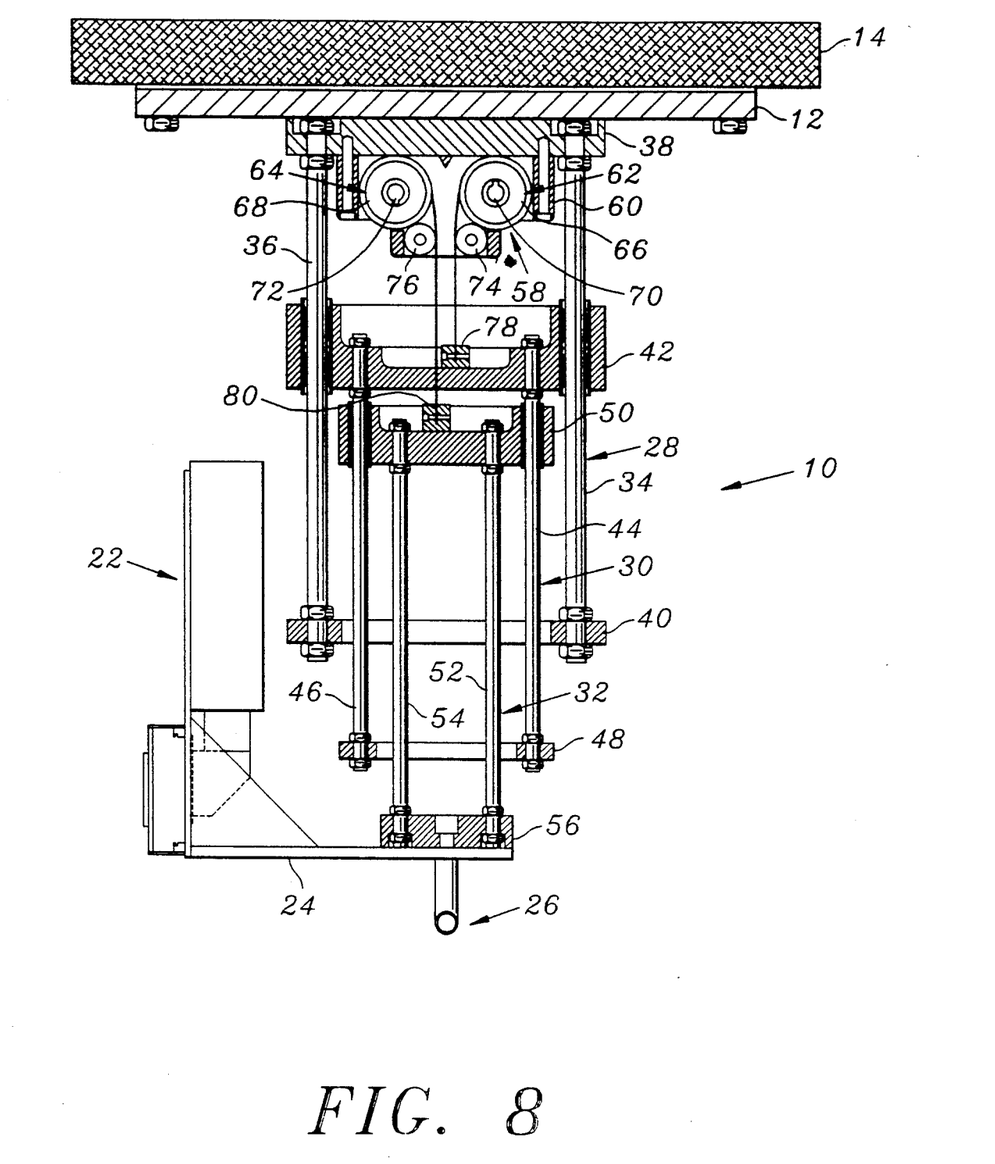
FIG. 8 is a sectional side view of the retractable support assembly of FIG. 3 taken in the direction of the arrows 8—8.

The inner construction of the assembly 10 is more clearly shown in FIGS. 2 and 8 which illustrate the assembly with the tubular cover 16, 18 and 20 removed from the structure of the assembly. As depicted, the tubular covers enclose three telescoping sets 28, 30 and 32 of three or more equally and laterally spaced and stabilized vertical guide rods. In FIGS. 2 and 8, for each of sets 28, 30 and 32, only two of the equally and laterally spaced vertical guide rods are shown for clarity of illustration. For set 28 vertical guide rods 34 and 36 are illustrated as being secured at their upper ends by locking nuts to a support plate 38 carried by the mounting plate 12. In this regard, the upper ends of the rods 34 and 36 are threaded and receive the locking nuts on opposite sides of the support plate 38 to firmly secure the upper ends of the rods to the support plate. The lower ends of the rods 34 and 36 are similarly threaded and secured by locking nuts to a horizontally or transversely extending annular tie plate 40. The tie plate 40 thus combines with the support plate 38 to provide a laterally stable three or more guide rod construction for the portion of the assembly extending from the stationary mounting plate 12.

In addition to the tie plate 40, the first set of guide rods 28 provide support for a horizontally or transversely extending carrier member 42 including openings aligned with and axially receiving the vertical guide rods of the set 28, including rods 34 and 36. Each of the vertical openings contains a vertical bearing such as those available from Thomson of Port Washington, N.Y. which define a low friction surface permitting smooth movement of the carrier member 42 up and down on the rods of the set 28.

The carrier member 42 provides support for the second set of vertical guide rods 30 as illustrated most clearly in FIG. 8. In this regard, of the rods comprising the set 30, only vertical guide rods 44 and 46 are illustrated in FIGS. 2 and 8. Like the rods 34 and 36, the vertical guide rods 44 and 46 are threaded at their upper and lower end. At their upper ends they pass through the carrier member 42 and are fixedly secured thereto by locking nuts bearing on the upper and lower surfaces of the carrier member.

To impart lateral stability to the guide rods comprising of set 30, an annular tie plate 48 extends horizontally or transversely between the lower ends of the rods. The tie plate 48 includes openings for vertically receiving the lower ends of the rods which are secured in place by locking nuts engaging the upper and lower surface of the tie plate. Thus, like the tie plate 40, the tie plate 48 combines with the carrier member 42 to provide a laterally stable second set of vertical guide rods 30 in the assembly 10.

In addition to the tie plate 48, the second set of vertical guide rods 30 supports a carrier member 50 including openings for vertically receiving the rods 44 and 46. Vertical bearings in the openings allow for smooth low friction movement of the carrier member 50 up and down on the rods comprising the second set of guide rods 30.

Like the carrier member 42, the carrier member 50 provides support for the third set of vertical guide rods 32. In this regard, of the equally and laterally spaced vertical guide rods comprising the set 32 only guide rods 52 and 54 are illustrated in FIGS. 2 and 8, and each include upper and lower threaded ends. The upper ends of the rods 52 and 54 pass through openings in the carrier member 50 and are secured in place by lock nuts bearing on the upper and lower surfaces of the carrier member. The threaded lower ends of guide rods 52 and 54 pass through openings in a horizontally or transversely extending tie plate 56 and are secured thereto by locking nuts bearing on its upper and lower surfaces. The tie plate 56 thus combines with the carrier member 50 to provide a laterally stable third set of vertical guide rods 32 in the assembly 10.

As illustrated in FIGS. 2 and 8, the support bracket 24 is secured to a bottom of tie plate 56 to support the image receptor 22 for movement in a vertical plane to a precisely determined and exact vertical stop position under control of the retractable support assembly 10. As previously stated, such up and down vertical movement of the assembly 10 is under control of an operator grasping the handle 26 which extends downwardly from the support bracket 24 secured to the tie plate 56.

In such vertical movement, the vertical guide rods comprising each of the sets 28, 30 and 32 telescope within each other. To accomplish this, the guide rods comprising the set 32 extend most closely to a central vertical axis of the assembly 10 in line with the handle 26 while the vertical guide rods comprising the set 30 are spaced slightly outwardly from the guide rods of the set 32. Similarly, the vertical guide rods comprising the set 28 are displaced slightly outwardly from the guide rods comprising the set 30. Thus, with vertical movement of the three sets of guide rods, the set 28 receives the set 30 which receives the set 32.

Figure 6:
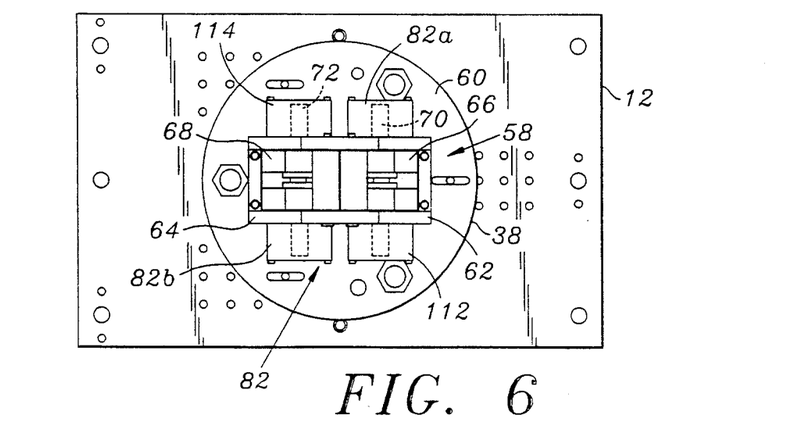
FIG. 6 is a view of the assembly shown in FIG. 2 looking along the arrows 6—6 to illustrate the connection of a stationary mount, vertical guide rods, and housing secured to the mount and containing an extension spring mechanism, fail safe brake and speed governor.
Figure 7:
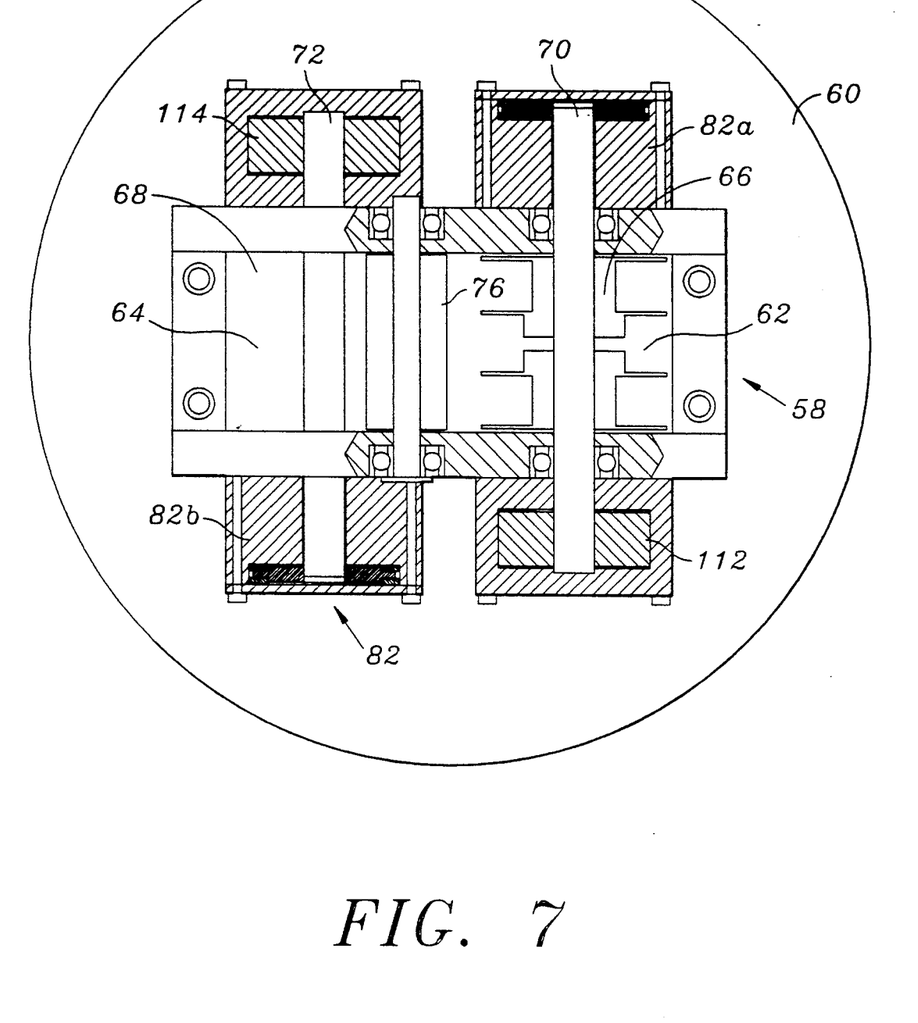
FIG. 7 is an enlargement of the central portion of FIG. 6 illustrating the extension springs comprising the extension spring mechanism and showing the fail safe brakes and speed governors in a cross-section.

As illustrated most clearly in FIGS. 6, 7, and 8, the vertical downward movement or extension of the telescoping sets of vertical guide rods is opposed by an extension spring mechanism 58 secured to the mounting plate 12 within the upper end of the set of guide rods 28. The extension spring mechanism 58 is mounted within a housing 60 and preferably comprises two (2) laterally spaced constant force extension springs 62 and 64 mounted on spools 66 and 68 with shafts 70 and 72 extending axially therefrom and secured for turning within the housing 60. Preferably, each of the extension springs 62 and 64 comprise a length of spring metal, such as Type 301 stainless steel having one end secured to its support spool and holes punched in its free end for connection to one of the carrier members. Such constant force extension springs are available from Ametek of Sellersville, Pa.

As illustrated in FIG. 8, the spools 66 and 68 are laterally spaced on opposite sides of the vertical axis of the assembly 10 with the free ends of the spring members extending from the spools over guide rollers 74 and 76 carried in the housing 60 for connection at 78 and 80 to the carrier members 42 and 50 respectively. The rollers may be covered with a rubber or other relatively soft material to reduce wear and vibration of the spring members. The extension springs normally hold the carrier members 42 and 50 and hence the sets of vertical guide rods 28, 30 and 32 in a vertically retracted position as illustrated in FIG. 8.

As previously indicated, to move the image receptor 22 to a predetermined vertical stop position, the operator grasps the handle 26 and pulls downwardly to move the sets of guide rods to the position illustrated in FIG. 2. In such movement, the set of guide rods 32 first moves downwardly until the carrier 50 engage the tie plate 40 for the set of guide rods 28. Continued downward movement moves the set 30 and the carrier member 42 downwardly until the carrier member 42 engages the tie plate 40 to define the exact vertical position desired for the image receptor 32.

Figure 10:
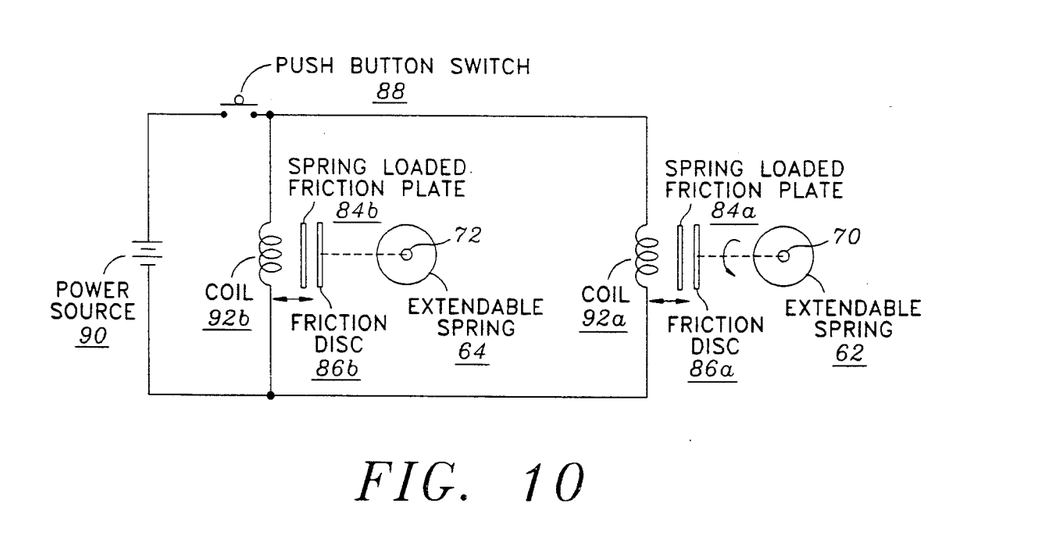
FIG. 10 is a circuit diagram of the electrical control for the fail safe brakes in controlling the extension spring mechanism.

Normally, such downward vertical movement of the telescoping sets of guide rods is prevented by a brake mechanism 82. The illustrated brake mechanism 82 comprises fail safe brakes 82a and b which respectively engage the shafts 70 and 72 to lock the extension spring mechanism 50 and prevent either extension or retraction of the extension spring 62 and 64. The brakes 82a and b are secured in the housing 60 on the shafts 70 and 72 and may comprise fail safe brakes manufactured by Warner of South Beloit, Ill. Such brakes feature a spline driven rotating friction disc clamped between spring loaded friction plates. An energizing of a coil overcomes the spring freeing the disc to rotate. Thus, as illustrated in the circuit of FIG. 10, for fail safe brakes 82a and b, friction plates 84a and b engage friction discs to normally prevent rotation of the shafts 70 and 72. However, with the closing of a switch 88, current from a power source 90 passes through coils 92a and b to overcome the spring forces and allow the friction discs and extension spring spools to rotate with a downward pulling on the extension springs coupled thereto. Preferably, in the assembly 10 of the present invention, the switch 88 comprises a push button located in the handle 26 which allows the operator to simultaneously release the brake mechanism 82 and pull down on the telescoping sets of guide rods to move the image receptor 22 to its desired exact vertical position. Once the image retractor is in that position, the operator may release the push button switch 88 to again engage the brakes 82a and b and lock the assembly 10 at the desired exact vertical position.

Figure 5:
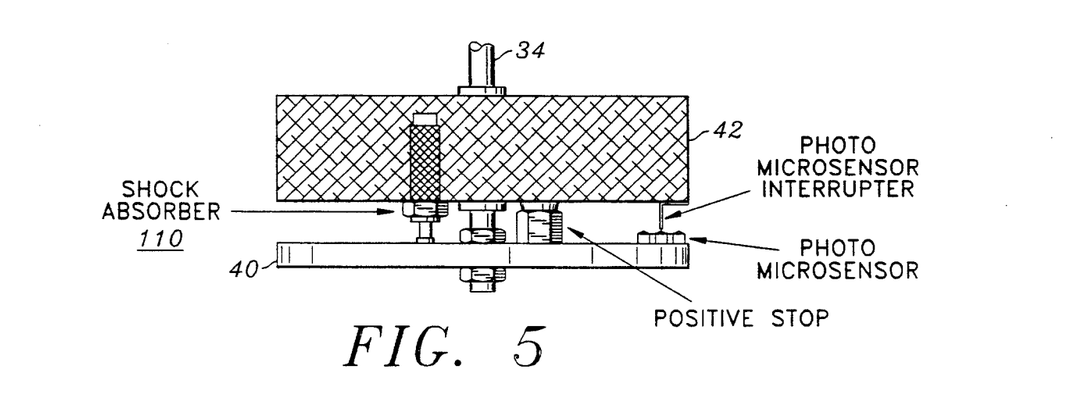
FIG. 5 is a fragmentary side view looking in the direction of the arrows 5—5 in FIG. 2 and showing a first carrier supported on vertical guide rods secured together by a tie plate and further illustrating a vertically adjustable stop, shock absorber, photomicrosensor interrupter and photomicrosensor.
Figure 9:
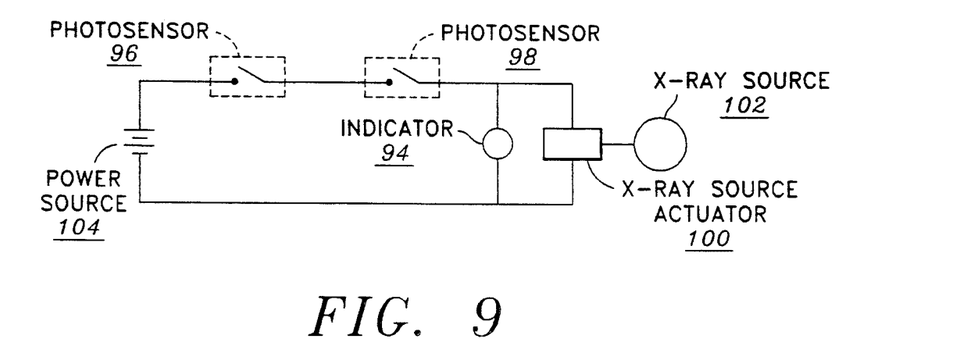
FIG. 9 is a circuit diagram of the sensor system for visually indicating when the support member is in its predetermined position.

To indicate the occurrence of such exact positioning of the image receptor, the assembly 10 preferably includes a visual indicator such as a light emitting diode 94 in circuit with photosensors 96 and 98 as illustrated in FIG. 9. As shown, a power source 104 is connected in series with the photosensors 96 and 98 as well as a conventional x-ray source actuator 100. When the assembly is in the exact predetermined vertical position, the photosensors are actuated to effect a closing of the electrical circuit to allow current to flow through to light the indicator and to energize the actuator 100. With the actuator energized, the x-ray source 102 remote from the image receptor may be operated to create an x-ray of the patient at the image receptor. In the structure of the assembly 10 illustrated in FIG. 5, such photosensors may comprise of a pair of photomicrosensors such as model EE-SG3M, available from OMRON of Schaumburg, Ill. One such photomicrosensor is illustrated in FIG. 5 as being carried by the tie plate 40 to receive a photomicrosensor interrupter extending from the carrier member 42. When the carrier member 42 engages the tie plate 40, the interrupter will affect a closing of the photosensor 96 illustrated in FIG. 9. A similar photomircosensor and photomicrosensor interrupter are respectively carried by the tie plate 48 and carrier member 50 to effect a closing of the photosensor switch 98 when the carrier member 50 engages with tie plate 48 as indicated. This completes the series circuit from the dc power source 104 through the photosensors 96 and 98 to energize the indicator 94 to provide a visual indication that the assembly 10 has reached the exact vertical position at which the x-ray source 102 may be activated.

The engaging of the tie plates 40 and 48 with their associated carrier members 42 and 50 respectively is defined by cooperative stops on the tie plates and carrier members. For example, FIG. 5 illustrates one of three such stops comprising a pad carried by the carrier member 42 to engage a vertically adjustable nut on the tie plate 40. Similar cooperative stops are carried by the tie plate 48 and carrier 50.

In moving to the cooperative stops, the carrier members 42 and 50 move smoothly on their associated guide rods in response to a downward pulling by the operator on the handle 26. Such smooth movement is only interrupted by the engaging of the cooperative stops which is cushioned by shock absorbers carried by the carrier members 42 and 50 as illustrated in FIG. 5 for the shock absorber 110. Such a shock absorber may be a self adjusting hydraulic shock absorber such as provided by Ace Controls of Farminton, Mich.

The smooth vertical up and down movement of the carrier members and sets of vertical guide rods is further enhanced in the preferred form of the assembly 10 by rotary viscous speed governors 112 and 114 on the ends of the shafts 70 and 72 opposite the fail safe brakes 82a and b. Such speed governors self regulate the rate of extension and contraction of the spring members from the extension spring mechanism 50 and may be of the type available from Vibratech of Buffalo, N.Y. Such speed governors ensure that the extension of the spring mechanism 50 is smooth both in extension and contraction to prevent undesired rapid downward movement of the telescoping sets of guide rods or undesired upward movement or backlash of the extension springs.

Thus, the retractable support assembly of the present invention meets the needs for a simplified, relatively inexpensive, laterally stable support assembly which is capable of being easily maneuvered and precisely controlled to bring the assembly to exact vertical stop positions. While a preferred form of such assembly has been described in some detail hereinabove, it is to be appreciated that changes and modifications may be made in the specifically illustrated assembly without departing from the spirit or scope of the present invention which is intended to be limited only by the terms of the following claims.

I claim:

1. A vertically retractable support assembly, comprising:
   mounting means;
   a first set of three or more laterally spaced guide rods secured to and extending vertically from the mounting means;
   first carrier means transverse to the first set of guide rods for vertically receiving the rods thereof to ride vertically thereon;
   a second set of three or more guide rods secured to and extending vertically from the first carrier means to support and vertically guide a member for selective vertical positioning by the support assembly;
   extension spring means secured to the mounting means and to the first carrier means for continuously urging the first carrier means upwardly toward a vertically retracted position with the second set of guide rods telescoped within the first set of guide rods;
   releasable brake means for normally preventing extension and retraction of the spring means;
   handle means for enabling an operator to exert vertical downward forces on the first carrier means in opposition to the spring means; and
   operator controllable means for selectively releasing the brake means to permit downward movement of the first and carrier means in response to the downward forces exerted by the operator to selectively and exactly position the member upon release of the operator controllable means whereby the member is held in such exact position by the normal operation of the brake means.

2. The assembly of claim 1 wherein the operator controllable means is mounted in the handle means whereby the operator can simultaneously release the brake means and pull down on the handle means.

3. The assembly of claim 1 further comprising:
   first tie means secured to extend transversely between lower ends of the rods of the first set of guide rods to provide lateral support therefor; and
   second tie means secured to extend transversely between lower ends of the rods of the second set of guide rods to provide lateral support therefor.

4. The assembly of claim 3 further comprising:
   first cooperative vertical stop means on the first carrier means and first tie means for stopping downward vertical movement of the first carrier means.

5. The assembly of claim 4 wherein the first stop means are vertically adjustable.

6. The assembly of claim 4 further comprising sensor means on the first and second tie means and first carrier means in circuit with an indicator means for actuating the indicator means when the member is in the exact vertical position.

7. The assembly of claim 4 further including shock absorbing means carried by the first carrier means for cushioning contact of the first and second stop means.

8. The assembly of claim 1 further comprising axial bearing means in the first carrier means for axially and smoothly receiving the rods of the first set of guide rods whereby minimal friction is generated upon movement of the first carrier means on the guide rods.

9. The assembly of claim 1 wherein:
   the spring means comprises a length of spring material secured at one end to a spool and coiled on the spool to extend therefrom in response to an axial pulling force exerted on a free end of the spring material; and
   the brake means is connected to the spool to normally prevent a turning of the spool and extension or retraction of the spring material.

10. The assembly of claim 9 further comprising a speed governor connected to the spool to smooth the rate of turning of the spool and extension and retraction of the spring material thereon.

11. The assembly of claim 1 further including second carrier means transverse to the second set of guide rods for vertically receiving the rods thereof to ride vertically thereon, and wherein the spring means comprises first and second extension springs each including a length of spring material secured at one end to a spool and coiled thereon to extend therefrom, each spool being supported in a housing secured to the mounting means with the spools laterally spaced therein and with free ends of the lengths of spring material connecting to the first and second carrier means respectively.

12. The assembly of claim 11 wherein the lengths of spring material extend over guide rollers carried in the housing.

13. The assembly of claim 12 wherein the guide rollers are coated with a cushioning material.

14. A vertically retractable support assembly, comprising:
   a plurality or laterally stabilized telescoping sets of three or more laterally spaced vertical guide rods each supporting a carrier for smooth low friction vertical movement on the rods thereof;
   an uppermost or first one of the sets of guide rods secured to a stationary mount to extend downward therefrom;
   a next uppermost or second one of the sets of guide rods secured to a first one of the carriers, that is the carrier supported on the first set of rods, to extend vertically downward therefrom and to telescope within the first set of of rods upon upward movement or retraction of the second set into the fist set;
   a second one of the carriers secured to the second set of guide rods to ride vertically thereon and for supporting a third one of the sets of guide rods to extend vertically downward therefrom and to telescope within the second set upon upward movement or retraction of the third set into the second set;
   a member to be precisely positioned carried by a lowermost one of the sets of guide rods;
   extension spring means secured to the mount and to the carriers for urging the carriers and the sets of guide rods toward a retracted position with the guide rods retracted;
   brake means for normally securing the spring means against extension and retraction; and
   operator controllable means for selectively releasing the brake means to allow the operator to smoothly lower the member to an exact vertical position.

15. The assembly of claim 14 wherein lateral stability is imparted to the guide rods by transverse tie means extending between lower ends of the rods comprising each set of rods.

16. The assembly of claim 15 wherein adjacent carriers and tie means carry stop means for engaging to define the exact stop position for the member.

* * * * *